(12) United States Patent
Ma et al.

(10) Patent No.: US 10,994,101 B2
(45) Date of Patent: May 4, 2021

(54) CATHETER ASSEMBLY WITH HIGH VISCOSITY LUBRICANT AND RELATED METHODS

(71) Applicant: Becton, Dickinson and Company, Franklin Lakes, NJ (US)

(72) Inventors: Yiping Ma, Layton, UT (US); Jeff O'Bryan, Murray, UT (US); Chad Alan Tagge, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 209 days.

(21) Appl. No.: 15/910,377

(22) Filed: Mar. 2, 2018

(65) Prior Publication Data

US 2019/0269889 A1 Sep. 5, 2019

(51) Int. Cl.
*A61M 25/06* (2006.01)
*A61M 25/00* (2006.01)
(Continued)

(52) U.S. Cl.
CPC ......... *A61M 25/0606* (2013.01); *A61L 29/14* (2013.01); *A61M 25/0009* (2013.01); *A61M 25/0043* (2013.01); *A61M 25/0097* (2013.01); *A61M 25/0631* (2013.01); *A61M 25/0693* (2013.01); *A61M 39/06* (2013.01); *A61M 39/0693* (2013.01); *A61M 25/0612* (2013.01);
(Continued)

(58) Field of Classification Search
CPC .......... A61M 25/0606; A61M 25/0612; A61M 25/0618; A61M 25/0009; A61M 25/0043; A61M 25/25; A61M 25/0097; A61M 25/0631; A61M 25/0693; A61M 2025/0062; A61M 2025/0046; A61M 39/0693; A61M 2039/062; A61M 2039/064; A61M 2039/066; A61M 2039/0036; A61M 2039/068; A61M 2039/0081; B23P 15/00; B21D 53/00; Y10T 29/49885

See application file for complete search history.

(56) References Cited

U.S. PATENT DOCUMENTS 9,789,280 B2 10/2017 Ma
2009/0105635 A1\* 4/2009 Bettuchi ............ A61B 17/3421
604/26

(Continued)

*Primary Examiner* — Jermie E Cozart
(74) *Attorney, Agent, or Firm* — Kirton & McConkie; Craig Metcalf; Kevin Stinger

(57) ABSTRACT

A method of preventing blood leakage through a septum of a catheter assembly when a needle is disposed within a slit of the septum may include providing a lubricant within multiple gaps disposed between an outer surface of the needle and the slit. The lubricant may include a viscosity greater than 1,000 centipoise. Providing the lubricant within the multiple gaps may include applying the lubricant to the outer surface of the needle, and inserting the lubricated needle distally through the slit of the septum. Providing the lubricant within the multiple gaps may include applying the lubricant to a tip of a septum actuator of the catheter assembly, and penetrating the septum with the lubricated septum actuator. Providing the lubricant within the plurality of gaps may include dispensing the lubricant within the slit of the septum prior to insertion of the septum into the lumen of the catheter adapter.

7 Claims, 9 Drawing Sheets

(51) Int. Cl.
*A61M 39/06* (2006.01)
*A61M 39/00* (2006.01)
*A61L 29/14* (2006.01)
*B23P 15/00* (2006.01)
*B21D 53/00* (2006.01)

(52) U.S. Cl.
CPC . *A61M 25/0618* (2013.01); *A61M 2025/0046* (2013.01); *A61M 2025/0062* (2013.01); *A61M 2039/0036* (2013.01); *A61M 2039/0081* (2013.01); *A61M 2039/062* (2013.01); *A61M 2039/064* (2013.01); *A61M 2039/066* (2013.01); *A61M 2039/068* (2013.01); *A61M 2205/0222* (2013.01); *B21D 53/00* (2013.01); *B23P 15/00* (2013.01); *Y10T 29/49885* (2015.01)

(56) References Cited

U.S. PATENT DOCUMENTS

| | | | |
|---|---|---|---|
| 2010/0137379 A1* | 6/2010 | Ou-Yang | A61L 29/085 514/358 |
| 2011/0160663 A1 | 6/2011 | Stout et al. | |
| 2013/0310764 A1* | 11/2013 | Burkholz | A61M 25/0045 604/246 |
| 2014/0228775 A1 | 8/2014 | Burkholz et al. | |
| 2014/0257234 A1* | 9/2014 | Ma | A61M 25/0043 604/172 |
| 2014/0364809 A1 | 12/2014 | Isaacson et al. | |
| 2017/0368314 A1 | 12/2017 | Isaacson | |

* cited by examiner

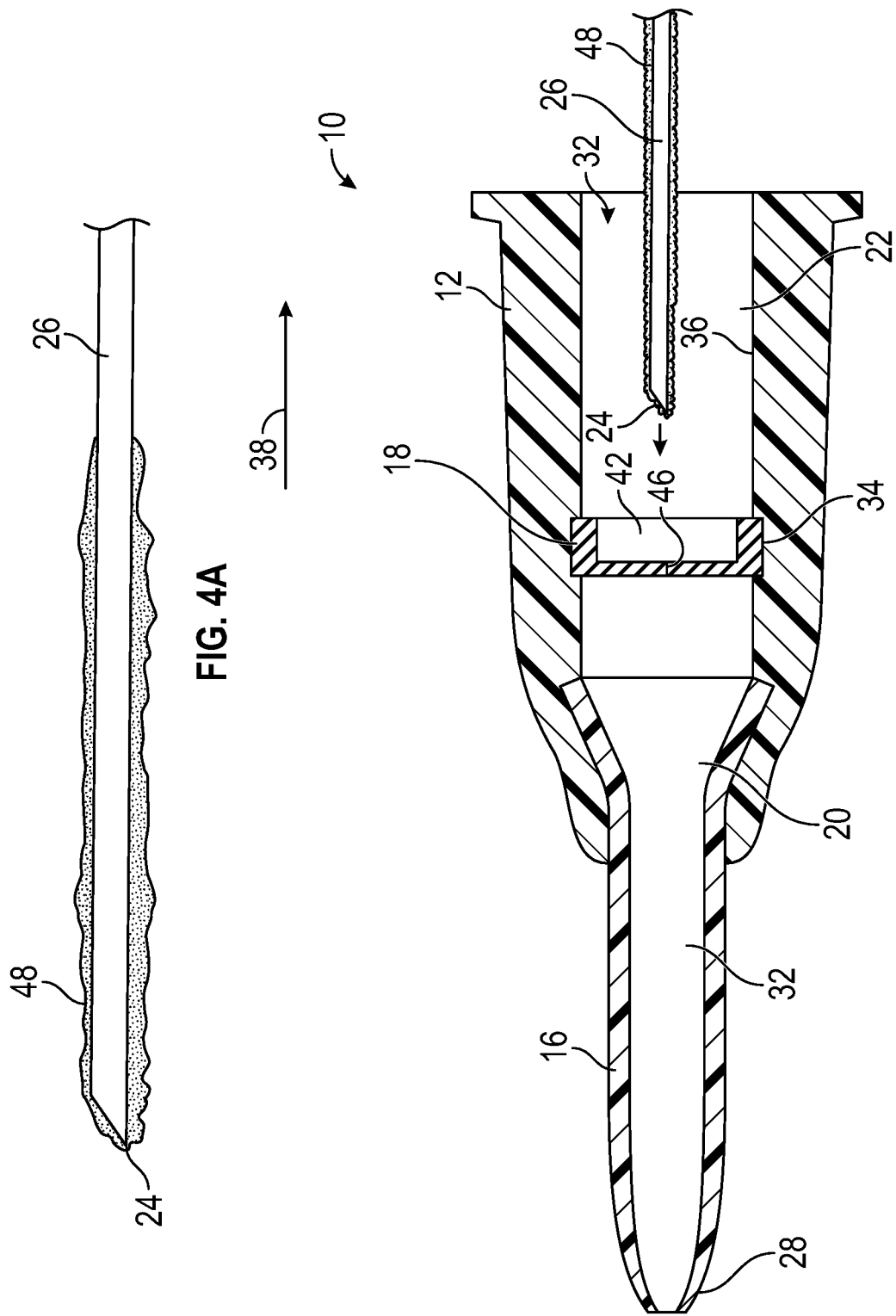

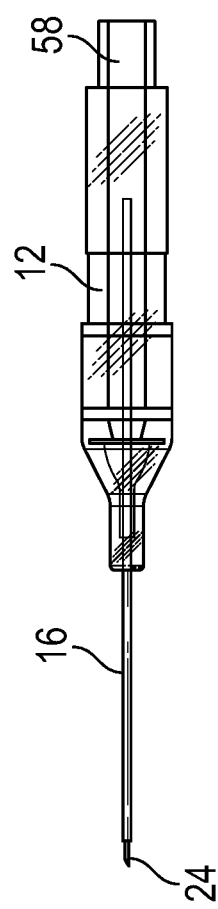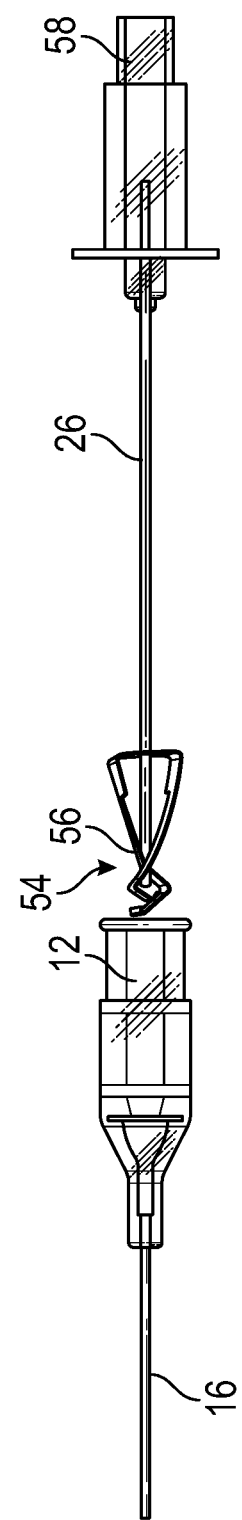
FIG. 6A
FIG. 6B

CATHETER ASSEMBLY WITH HIGH VISCOSITY LUBRICANT AND RELATED METHODS

BACKGROUND OF THE INVENTION

Once placement of an introducer needle within a blood vessel of a patient has been confirmed, a clinician may temporarily occlude flow in the blood vessel and remove the introducer needle, leaving a catheter in place within the blood vessel. In some instances, the clinician may also attach a device to the catheter for fluid infusion and/or blood withdrawal. This process has been somewhat difficult in practice since many catheter placement sites simply do not allow easy occlusion of the blood vessel. Additionally, even when such occlusion is achieved, it may be imperfect, resulting in blood leaking from a catheter assembly that houses the catheter, which may endanger the clinician.

Catheter assemblies have thus been provided in the art that provide a variety of seals or "septa" for preventing outflow of fluid during and following removal of the introducer needle from the blood vessel. A septum may be secured within the catheter assembly via friction and/or adhesive between the septum and a wall of the catheter assembly.

However, when the needle is completely withdrawn from the septum, substantial blood leakage through the septum may occur. Thus, in some instances, when the catheter is placed within the blood vessel, the clinician may only partially withdraw the needle and leave the needle within the slit of the septum, which may be referred to as "parking" the needle, in an attempt to avoid the substantial blood leakage that may occur on complete withdrawal of the needle. When the needle is parked or partially withdrawn and disposed within a slit of the septum, there may still be some blood leakage through the slit of the septum, because the slit may not conform perfectly to an outer surface of the needle. Accordingly, there is a need in the art for devices, systems, and methods that prevent blood leakage through the slit of the septum when the needle is in the slit.

BRIEF SUMMARY OF THE INVENTION

The present disclosure relates generally to a catheter assembly that includes a lubricant, as well as related devices and methods. In some embodiments, the lubricant may include a high viscosity lubricant, such as, for example, greater than 1,000 centipoise, which may facilitate blood control. In some embodiments, the lubricant may prevent blood from penetrating a septum of the catheter assembly when a needle of the catheter assembly is disposed within a slit of the septum. In further detail, in some embodiments, the lubricant may be disposed within multiple gaps disposed between an outer surface of the needle and the slit of the septum, which may prevent blood leakage through the septum when the needle is disposed within the slit of the septum.

In some embodiments, the catheter assembly may include a catheter adapter, which may include a distal end, a proximal end, and a lumen extending between the distal end and the proximal end. In some embodiments, the septum may be disposed within the lumen of the catheter adapter. In some embodiments, the needle may be disposed within the lumen of the catheter adapter. In some embodiments, the catheter assembly may include a catheter, which may extend distally from the distal end of the catheter adapter. In some embodiments, the catheter assembly may include a septum actuator, which may be configured to penetrate the septum in response to insertion of a medical device into the proximal end of the catheter adapter.

In some embodiments, a method of manufacturing the catheter assembly to prevent blood leakage through the septum when the needle is disposed within the slit of the septum may include providing the lubricant within the gaps disposed between the outer surface of the needle and the slit of the septum. In some embodiments, providing the lubricant within the gaps disposed between the outer surface of the needle and the slit of the septum may include applying the lubricant to the outer surface of the needle prior to insertion of the needle into the slit of the septum and/or inserting the lubricated needle distally through the slit of the septum. In some embodiments, in response to insertion of the lubricated needle distally through the slit of the septum, the lubricant may be deposited within the gaps. In some embodiments, in response to insertion of the lubricated needle distally through the slit of the septum, at least a portion of the lubricant may be transferred from the needle to the gaps due to contact between the lubricant on the needle and the slit.

In some embodiments, applying the lubricant to the outer surface of the needle prior to insertion of the needle into the slit of the septum may include applying the lubricant to a portion of the outer surface of the needle. In some embodiments, the portion of the outer surface of the needle may be configured to be disposed within the slit of the septum when the needle is in an insertion position for insertion into the patient. In some embodiments, the needle may extend beyond a distal end of the catheter when the needle is in the insertion position.

In some embodiments, providing the lubricant within the gaps disposed between the outer surface of the needle and the slit of the septum may include applying the lubricant to a distal tip of the septum actuator prior to insertion of the septum actuator into the slit of the septum and/or inserting the lubricated septum actuator into the septum. In some embodiments, in response to inserting the lubricated septum actuator into the septum, the lubricant may be deposited within the slit. In some embodiments, in response to movement of the septum actuator through the slit, at least a portion of the lubricant may be transferred to the gaps due to contact between the lubricant on the septum actuator and the slit.

In some embodiments, providing the lubricant within the gaps disposed between the outer surface of the needle and the slit of the septum may include dispensing the lubricant within the slit of the septum prior to insertion of the septum into the lumen of the catheter adapter during manufacture.

In some embodiments, the slit of the septum may include various shapes and sizes. In some embodiments, any number of gaps may be formed in response to the needle being disposed within the slit. In some embodiments, the slit may be Y-shaped and may include exactly three gaps. In some embodiments, the slit may be linear and may include exactly two gaps.

In some embodiments, the lubricant may include a water-insoluble lubricant. In some embodiments, the lubricant may include a gel lubricant. In some embodiments, the lubricant may include an oil lubricant, such as, for example, polydimethyl siloxane, polytrifluoropropylmethyl siloxane, or a copolymer of dimethylsiloxane and trifluoropropylmethylsiloxane. In some embodiments, the lubricant may include an antimicrobial and/or an anti-thrombogenic agent to decrease the likelihood of blood clots within the catheter assembly.

In some embodiments, a method of operating the catheter assembly may include inserting the needle of the catheter assembly into vasculature of a patient. In some embodiments, in response to inserting the needle into the vasculature of the patient, blood flashback may occur between the outer surface of the needle and an inner surface of the catheter. In some embodiments, the lubricant disposed within the gaps may prevent the blood flashback from penetrating the septum when the needle is disposed within the slit of the septum.

In some embodiments, the catheter assembly may include a passive needle safety mechanism. In some embodiments, the method of operating the catheter may further include partially withdrawing the needle through the passive needle safety mechanism such that a distal tip of the needle is disposed between a distal end of the catheter and the septum. In these and other embodiments, the needle may extend through the septum when the needle is partially withdrawn, and the lubricant disposed within the gaps may prevent blood disposed on an outer surface of the distal tip of the needle from penetrating the septum.

It is to be understood that both the foregoing general description and the following detailed description are exemplary and explanatory and are not restrictive of the invention, as claimed.

BRIEF DESCRIPTION OF THE SEVERAL VIEWS OF THE DRAWINGS

Example embodiments will be described and explained with additional specificity and detail through the use of the accompanying drawings in which:

FIG. 4A is a longitudinal cross-sectional view of the needle having a lubricant applied to an outer surface of the needle, according to some embodiments;

FIG. 4B is a longitudinal cross-sectional view of the catheter assembly during an example manufacturing process, illustrating the needle being inserted into a proximal end of an example catheter adapter and through an example septum, according to some embodiments;

FIG. 6A is an upper perspective view of the catheter assembly having an example needle shield mechanism, according to some embodiments;

FIG. 6B is an upper perspective view of the catheter assembly having the needle shield mechanism removed from the catheter adapter.

DETAILED DESCRIPTION OF THE INVENTION

The present disclosure relates generally to a catheter assembly that includes a lubricant, as well as related devices and methods. In some embodiments, the lubricant may include a high viscosity lubricant, which may act as a blood barrier and facilitate blood control. In some embodiments, the lubricant may prevent blood from penetrating a septum of the catheter assembly when an introducer needle of the catheter assembly is disposed within a slit of the septum. In further detail, in some embodiments, the lubricant may be disposed within multiple gaps disposed between an outer surface of the needle and the slit of the septum, which may prevent blood leakage through the septum when the needle is disposed within the slit of the septum.

As used in the present disclosure, the term "distal" refers to a portion of the catheter assembly or component thereof that is farther from a user, and the term "proximal" refers to a portion of the catheter assembly or component thereof that is closer to the user. As used in the present disclosure, the term "user" may refer to a clinician, doctor, nurse, or any other care provider and may include support personnel.

Figure 1A:
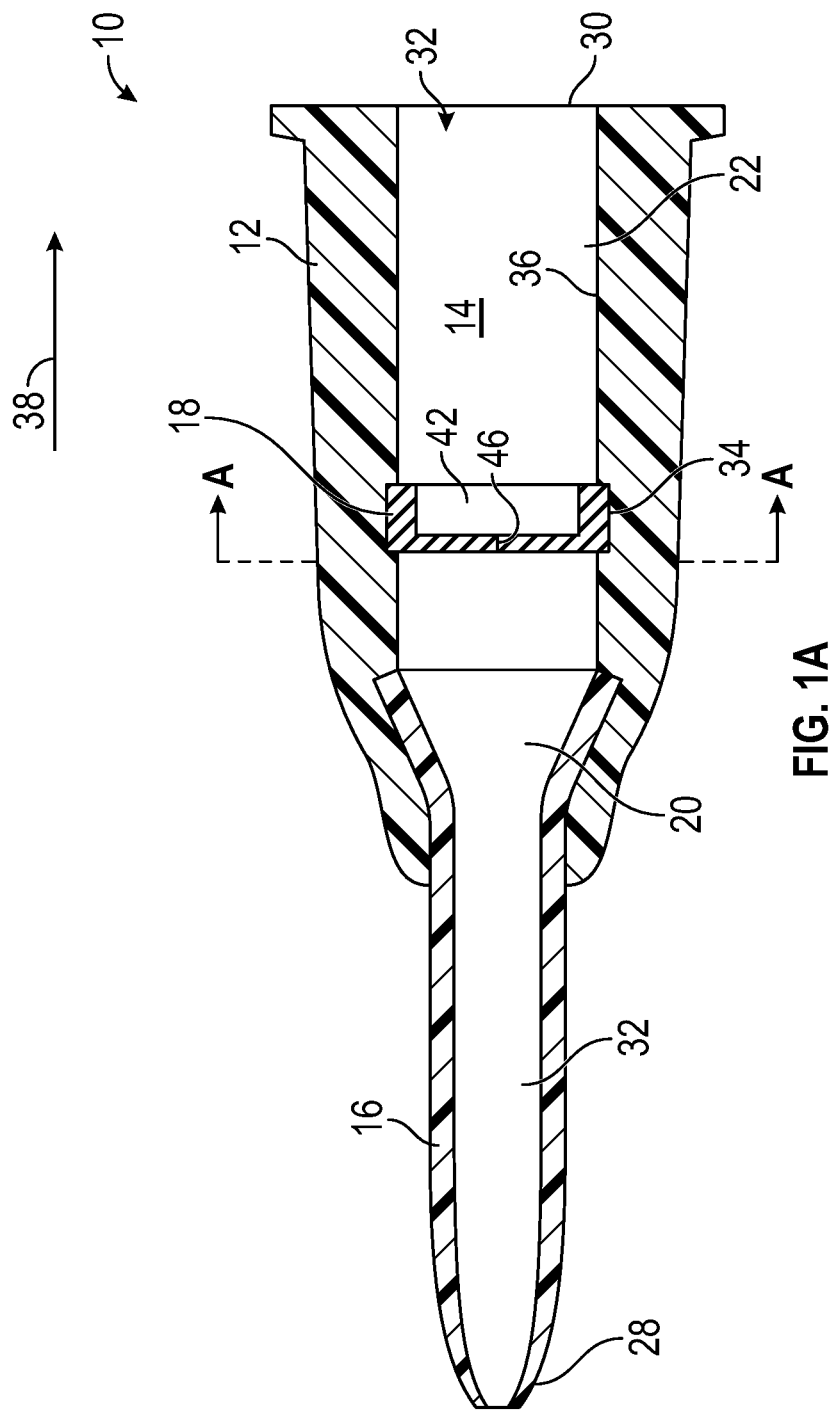
FIG. 1A is a longitudinal cross-sectional view of an example catheter assembly with a needle removed, according to some embodiments.
Figure 1B:
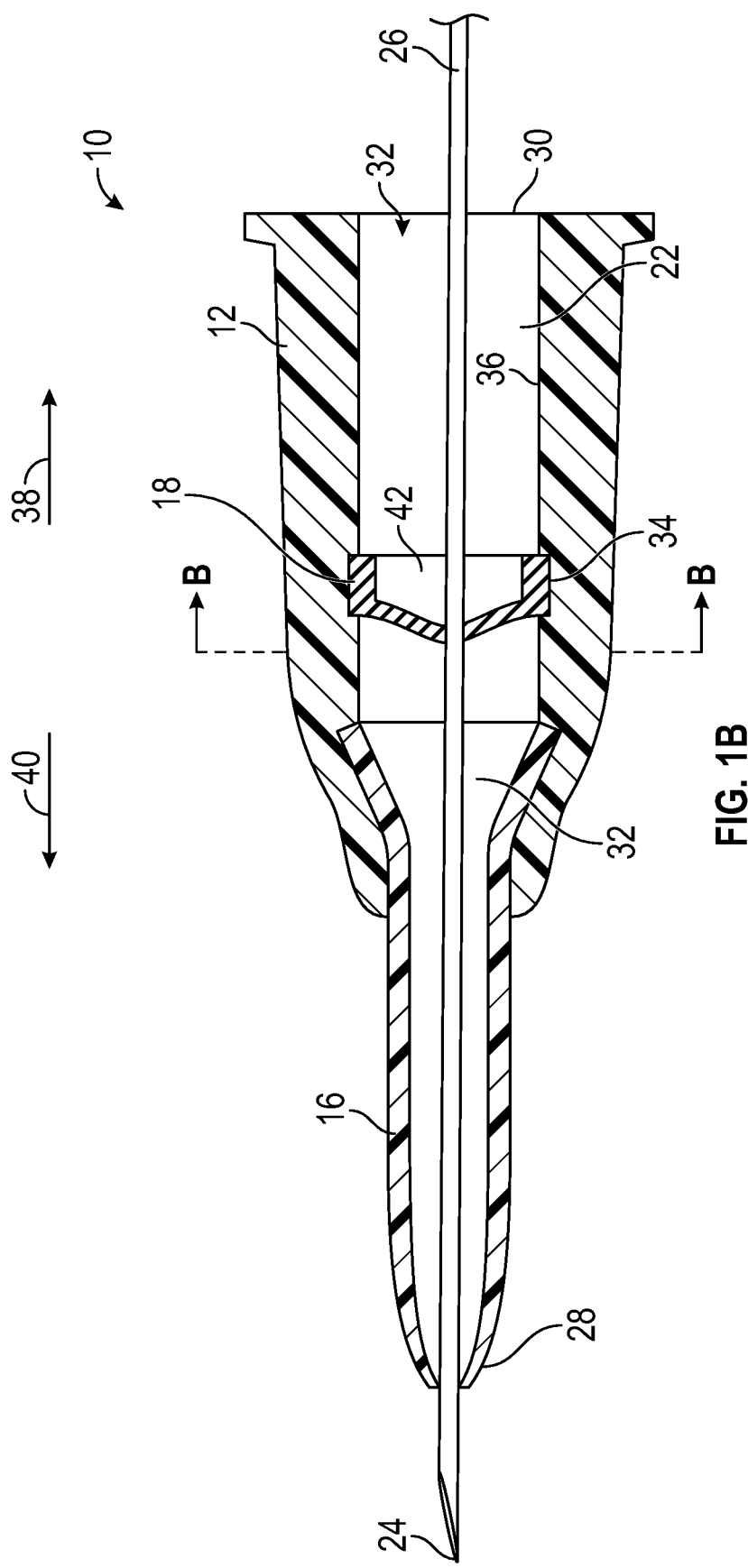
FIG. 1B is a longitudinal cross-sectional view of the catheter assembly, illustrating an example needle in an insertion position, according to some embodiments.

Referring now to FIGS. 1A-1B, the catheter assembly 10 may provide access to vasculature of a patient, such as for infusion therapy procedures or blood collection. In some embodiments, the catheter assembly 10 may include a catheter adapter 12, which may include a distal end, a proximal end, and a lumen 14 extending between the distal end and the proximal end. In some embodiments, the catheter assembly 10 may include an catheter 16, which may include a peripheral intravenous catheter, in fluid communication with the catheter adapter 12. In some embodiments, the catheter 16 may extend distally from the distal end of the catheter adapter 12.

In some embodiments, catheter adapter 10 may include a blood control septum 18, which may act as a physical barrier to control the flow of blood and other fluids between a distal chamber 20 and a proximal chamber 22 of catheter adapter 12. In some embodiments, the septum 18 may be disposed within the lumen 14 of the catheter adapter 12. In some embodiments, in response to insertion of a distal and/or beveled tip 24 of the introducer needle 26 and a distal tip 28 of the catheter 16 into the vasculature of the patient and the removal of the needle 26, blood from the patient may flow through lumen 30 of the catheter 16 and into the distal chamber 20. In these and other embodiments, the blood may be prevented from bypassing the septum 18 due to presence of the lubricant 48 within the gaps disposed between an outer surface of the needle 26 and a slit 46 of the septum 18. Otherwise, the septum 20 may substantially prevent blood from bypassing the septum 18 when the needle 26 is disposed within the slit 46 of the septum 18, but some leakage may occur, posing a hazard to a user.

FIG. 1A illustrates the catheter assembly 10 prior to complete manufacture of the catheter assembly 10 such that the needle 26 has not yet been inserted through the catheter adapter 12, according to some embodiments. In some embodiments, the needle may also be removed from the catheter adapter 12 after the catheter 16 has been placed within the vasculature of the patient. FIG. 1B illustrates the catheter assembly 10 ready for clinical use, having the needle 26 disposed in an insertion position for insertion into a patient, according to some embodiments. In these and other embodiments, the tip 24 of the needle 26 may extend beyond a distal tip of the catheter 20. In some embodiments, the needle 26 may be disposed within the lumen 14 of the catheter adapter 12.

In some embodiments, the catheter assembly 10 may include a needle hub (illustrated, for example, in FIGS. 6A-6B), which may support the needle 26. In some embodiments, the needle 26 may be positioned through the catheter adapter 12 and the catheter 16 such that the tip 24 of the needle 26 extends beyond the distal tip 28 of the catheter 16. In some embodiments, the tip 24 may provide a cutting surface whereby to penetrate skin of the patient and provide access to the vasculature.

In some embodiments, the septum 18 may be seated in an annular groove 34 that is provided in an inner surface 36 of the catheter adapter 12. In some embodiments, the septum 18 may include an outer diameter that is greater than a diameter of the fluid pathway 32 and/or a diameter of the annular groove 34. Thus, the septum 18 may be secured in the fluid pathway 32 and/or the annular groove 34 and may be prevented from moving within the fluid pathway 38 in a proximal direction 38 and/or distal direction 40. In some embodiments, an outer edge of the septum 18 may be secured to inner surface 36 via an adhesive, plastic weld, retainer clip, or other mechanical connection.

In some embodiments, the septum 18 may include various shapes and configurations. For example, in some embodiments the septum 18 may include a disc. As another example, in some embodiments, the septum 18 may include a cylinder having a proximal opening 42. In some embodiments, the septum 18 may include the slit 46 or multiple slits that may form a pathway through the septum 18. In some embodiments, a distal end of the slit 46 may be disposed at a distal face of the septum 18, a proximal end of the slit 46 may be disposed at a proximal face of the septum 18, and an inner portion of the slit 46 may extend from the distal face to the proximal face through an inner surface of the septum 18. In some embodiments, the slit 46 may be configured to permit passage of the needle 26 through the septum 18. In some embodiments, a resilient or elastic nature of the septum 18 may allow the slit 26 to stretch and thereby accommodate passage of the needle 26.

Figure 2A:
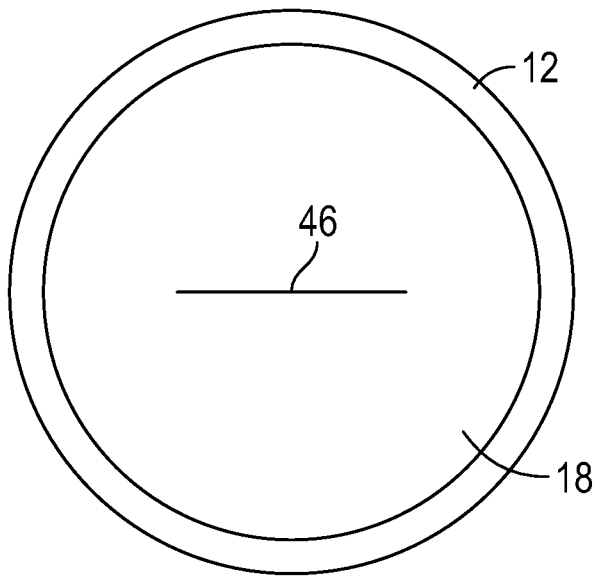
FIG. 2A is a cross-sectional view of the catheter assembly along the line A-A of FIG. 1A, according to some embodiments.
Figure 2B:
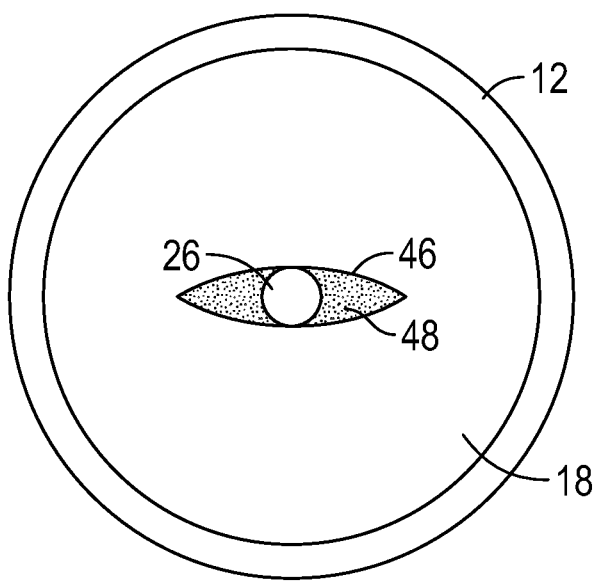
FIG. 2B is a cross-sectional view of the catheter assembly along the line B-B of FIG. 1B, according to some embodiments.
Figure 3A:
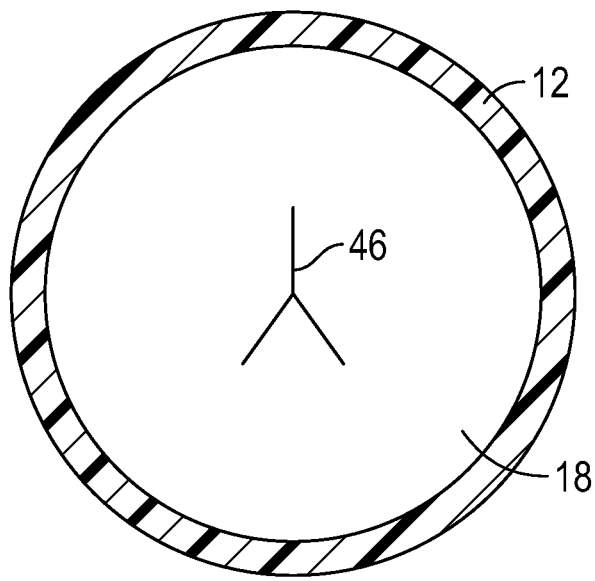
FIG. 3A is an alternative cross-sectional view of the catheter assembly along the line A-A of FIG. 1A, according to some embodiments.
Figure 3B:
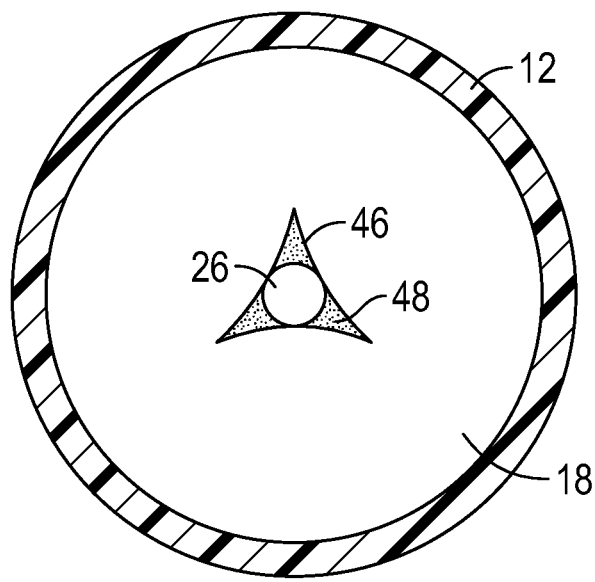
FIG. 3B is an alternative cross-sectional view of the catheter assembly along the line B-B of FIG. 1B, according to some embodiments.

In some embodiments, the slit 46 of the septum 18 may include various shapes and configurations. In some embodiments, any number of gaps may be formed in response to the needle 26 being disposed within the slit 46. Referring now to FIGS. 2A-2B, in some embodiments, the slit 46 may be linear, for example, and include exactly two gaps when the needle 26 is disposed within the slit 46. Referring now to FIG. 3A-3B, in some embodiments, the slit 46 may be Y-shaped, for example, and include exactly three gaps when the needle 26 is disposed within the slit 46. In some embodiments, the slit 46 may be X-shaped, for example, which may result in four gaps when the needle 26 is disposed within the slit 46.

Referring collectively to FIGS. 2B and 3B, in some embodiments, the lubricant 48 may be provided within the gaps. In some embodiments, the lubricant 48 may include a high viscosity lubricant. In some embodiments, the viscosity of the lubricant may be high enough to prevent blood from flowing through the gaps in which the lubricant 48 is disposed. Thus, in some embodiments, the lubricant 48 may prevent blood from flowing from the distal chamber 20 to the proximal chamber 22 through the gaps when the needle 26 is disposed within the slit 46.

In some embodiments, the viscosity of the lubricant 48 may be greater than 100 centipoise. In some embodiments, a viscosity less than 100 centipoise may not be great enough to prevent blood from flowing through the gaps in which the lubricant 48 is disposed. In a preferred embodiment, the viscosity of the lubricant 48 may be greater than or equal to 1,000 centipoise, which may facilitate sealing the gaps and the septum 18 when the needle 26 is disposed within the slit 46. In some embodiments, the viscosity of the lubricant may be between 1,000 centipoise and 2,000,000 centipoise, inclusive. In some embodiments, the lubricant 48 may include one or more of the following: a gel, an oil, an antimicrobial agent, a fugitive solvent, an alcohol, and an anti-thrombogenic agent, as will be explained in further detail.

In some embodiments, the lubricant 48 may be insoluble in blood and/or most infusates, and thus may stay within the gaps during multiple procedures, such as for example, blood drawings, drug infusion, total parenteral nutrition (TPN) procedures, and saline and heparin flushes.

In some embodiments, the lubricant 48 may include a viscous gel. In some embodiments, the lubricant 48 may be shapeable. In some embodiments, the lubricant 48 may include one or more oils. In some embodiments, the oils may include silicon, polydimethyl siloxane, polytrifluoropropylmethyl siloxane, a copolymer of dimethylsiloxane and trifluoropropylmethylsiloxane, or another suitable oil lubricant. In some embodiments, a solvent may be added to the oil lubricant to facilitate application of the lubricant 48.

In some embodiments, the lubricant 48 may include one or more antimicrobial agents, which may prevent colonization and growth of microbes and pathogens within the catheter assembly 10. In some embodiments, the antimicrobial agents may include solid particles that are insoluble in the lubricant 48 or in liquid form. In some embodiments, the antimicrobial agents may be well mixed within the lubricant 48 prior to application of the lubricant 48 to the needle 26 and/or a septum actuator, as will be explained in further detail.

In some embodiments, the lubricant 48 may include one or more fugitive solvents, such as, for example, tetrahydrofuran (THF), methylethylketone (MEK), a hexane solvent, or another suitable solvent. In some embodiments, the lubricant 48 may include a fugitive solvent in an amount approximately equal to 70% (w/v) of lubricant 48.

In other embodiments, the lubricant 48 may include one or more alcohols. In some embodiments, the lubricant 48 may include a lower alcohol having between one and six carbons (C1-C6). In some embodiments, the alcohol component may include one or more of the following: ethyl alcohol, isopropanol, propanol, and butanol. In some embodiments, lubricant 48 may include an alcohol component in an amount approximately equal to 40% (w/v) of lubricant 48. In other embodiments, the lubricant 48 may include an alcohol component in an amount from approximately 20% (w/v) to approximately 95% (w/v).

In some embodiments, the lubricant 48 may include an anti-thrombogenic agent. In some embodiments, the anti-thrombogenic agent may decrease a likelihood of blood clotting within the catheter assembly 10. In some embodiments, the anti-thrombogenic agent may decrease the likelihood of blood clots on any surface coated by lubricant 48.

Referring now to FIG. 4A-4B, in some embodiments, the lubricant 48 may be provided in the gaps by applying the lubricant 48 to the outer surface of the needle 26 prior to insertion of the needle 26 into the slit 46 of the septum 18. In some embodiments, the lubricated needle 26 may then be inserted through the slit 46 to deposit the lubricant 48 within the gaps. In some embodiments, the lubricated needle 26 may be inserted distally through the slit 46, as illustrated, for example, in FIG. 4B, or proximally through the slit 46.

In some embodiments, the lubricant 48 may be applied to the outer surface of the needle 26 by dipping, brushing, spraying, or any other suitable techniques known in the art. In some embodiments, the lubricant 48 may be applied to the outer surface of the needle 26 prior to fully manufacturing the catheter assembly 10 or placing the needle 26 within the catheter assembly 10. In some embodiments, upon inserting the needle 26 into the catheter adapter 12 and the slit 46 of the septum 18, the lubricant 48 may rub against the inner portion of the slit 46, thereby depositing the lubricant 48 in the gaps. In some embodiments, the needle 26 may be inserted through the septum 18 without providing an enlarged pathway through the septum 18. For example, a threader may not be used. In this way, the lubricant 48 may be displaced from the outer surface of the needle 26 during manufacture or assembly of the catheter assembly 10, according to some embodiments.

In some embodiments, the lubricant 48 may be applied to one or more portions of the outer surface of the needle 26. In some embodiments, the lubricant 48 may be applied to an entire outer surface of the needle 26. In some embodiments, the lubricant 48 may be applied to the tip 24 of the needle 26. In some embodiments, the lubricant 48 may be applied to a portion of the outer surface of the needle 26 configured to be disposed within the slit 46 of the septum 18 when the needle 26 is in the insertion position for insertion into the patient. In some embodiments, the lubricant 48 may be only applied to the portion of the outer surface of the needle 26 configured to be disposed within the slit 46 of the septum 18 when the needle 26 is in the insertion position, which may limit excess lubricant 48 within the catheter adapter 12.

In some embodiments, the lubricant 48 disposed in the gaps may prevent passage of fluid from distal chamber 20 to proximal chamber 22 when the needle 26 is moved in the proximal direction 38. In some embodiments, upon complete removal of needle 26 from the slit 46, slit 46 may self-close, thereby preventing fluid within distal chamber 20 from passing into the proximal chamber 22.

In some embodiments, the catheter assembly 10 may be manufactured such that the needle 26 positioned in the insertion position and coated with the lubricant 48 distal to the septum 18. In these and other embodiments, the lubricant 48 may be absent from the gaps disposed between the outer surface of the needle 26 and the slit 46 of the septum 18. In some embodiments, prior to use of the catheter assembly 10, the user may partially withdraw the needle 26 through the septum 18 to deposit the lubricant within the gaps.

Figure 5A:
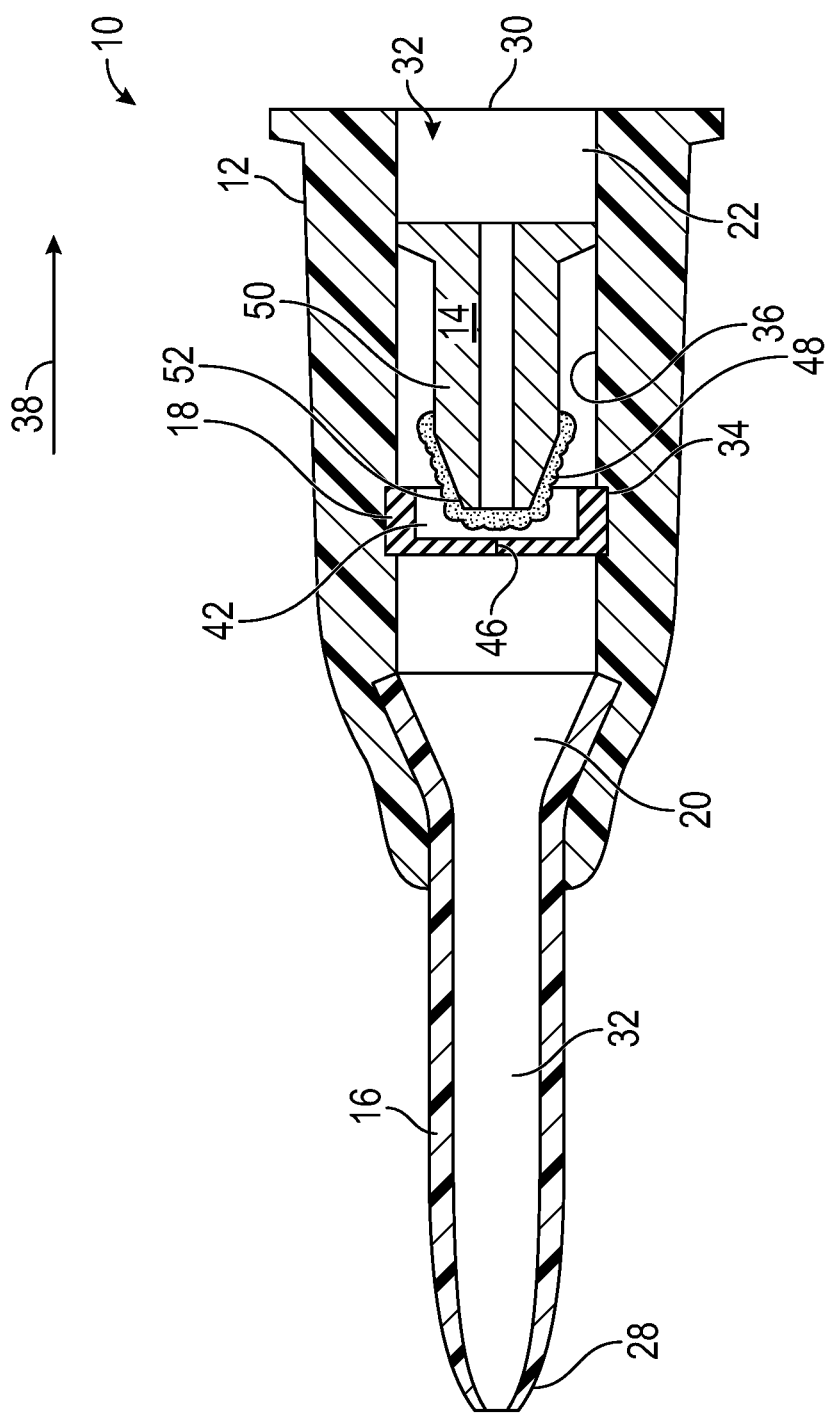
FIG. 5A is a longitudinal cross-sectional view of the catheter assembly having an example septum actuator, according to some embodiments.
Figure 5B:
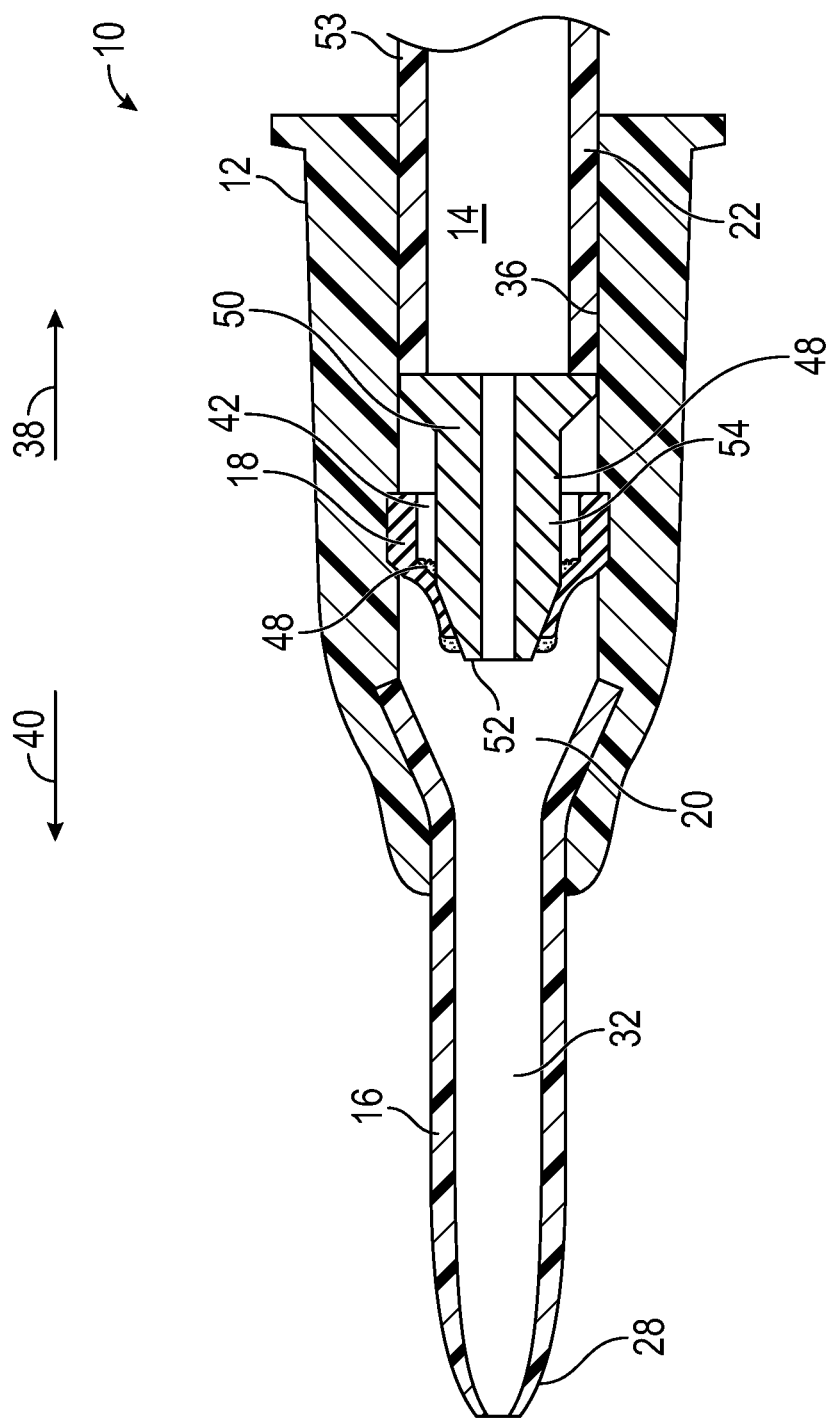
FIG. 5B is a longitudinal cross-sectional view of the septum actuator inserted through the septum, according to some embodiments.

Referring now to FIGS. 5A-5B, in some embodiments, the catheter assembly 10 may include the septum actuator 50. In some embodiments, the lubricant 48 may be applied to the outer surface of the septum actuator 50 by dipping, brushing, spraying, or any other suitable techniques known in the art. In some embodiments, the lubricant 48 may be applied to the outer surface of the septum actuator 50 prior to fully manufacturing the catheter assembly 10 or placing the septum actuator 50 within the catheter assembly 10. In some embodiments, upon inserting the septum actuator 50 into the catheter adapter 12 and the slit 46 of the septum 18, the lubricant 48 may rub against the inner portion of the slit 46, thereby depositing the lubricant 48 in the inner portion of the septum 18. Thus, in some embodiments, when the needle 26 is inserted through the slit 46, the lubricant 48 may already be disposed within the slit 46 and may fill the gaps.

In some embodiments, the lubricant 48 may be applied to one or more portions of the outer surface of the septum actuator 50. In some embodiments, the lubricant 48 may be applied to an entire outer surface of the septum actuator 50. In some embodiments, the lubricant 48 may be applied to a tip 52 of the septum actuator 50. In some embodiments, the lubricant 48 may be applied to a portion of the outer surface of the septum actuator 50 configured to be disposed within the slit 46 of the septum 18 when the septum actuator 50 is moved distally in response to insertion of another medical device 53 or an assembly tool into the proximal end of the catheter adapter 12. In some embodiments, the tip 52 of the septum actuator 50 may be disposed touching and proximate a proximal face of the septum 18 or may be spaced apart from the proximal face of the septum 18 when the medical device 52 is absent from the catheter adapter 12.

In some embodiments, prior to use of the catheter assembly 10, the user may insert the septum actuator 50 through the slit 46 to deposit the lubricant within the gaps. In these and other embodiments, the catheter assembly 10 may be manufactured without the lubricated disposed within the gaps.

Figure 6C:
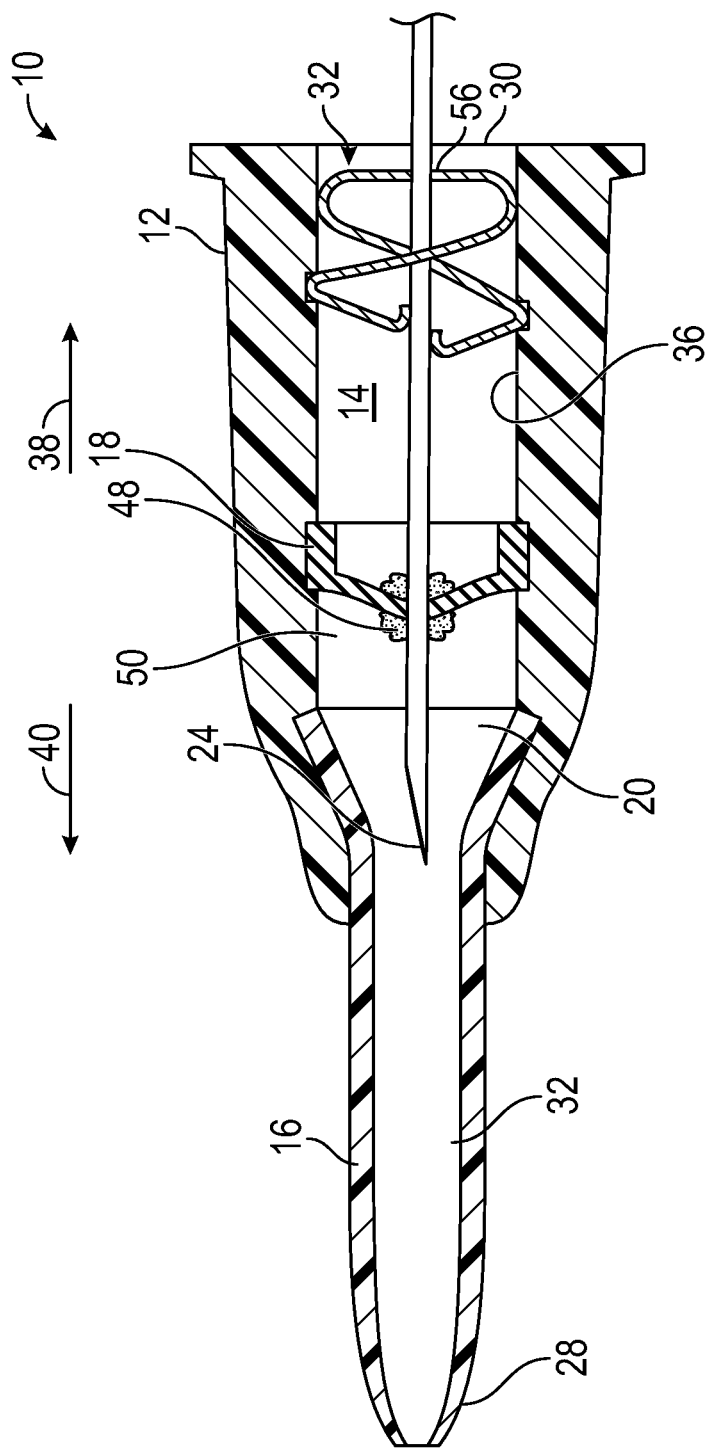
FIG. 6C is a longitudinal cross-sectional view of the catheter assembly, illustrating the needle partially withdrawn, according to some embodiments.

Referring now to FIGS. 6A-6C, in some embodiments, the catheter assembly 10 may include a needle shield or safety mechanism 54. Any suitable type of needle shield mechanism 54 is contemplated. In some embodiments, the needle shield mechanism 54 may be passive, meaning any needle shield mechanism 54 that automatically shields the needle 26 when the needle 26 is proximally withdrawn from the patient and at least a portion of the catheter adapter 12. In some embodiments, with a passive needle shield mechanism 54, there is no user activation of the needle shield mechanism 54 besides proximal withdrawal of the needle 26 from at least a portion of the catheter adapter 12. For example, there may be no pushing of a button, twisting, or clicking of the catheter assembly 10 to activate the needle shield mechanism 54. In some embodiments, the passive needle shield mechanism 54 may be engaged during proximal withdrawal of the needle 26 with respect to the catheter assembly 10. In some embodiments, the needle shield mechanism 54 may be active, meaning the user activates the needle shield mechanism 54 in a manner other than or in addition to physically and proximally withdrawing the needle 26 from at least a portion of the catheter adapter 12 to shield the distal tip of the needle 26 within the needle shield mechanism 54. For example, an active needle shield mechanism 54 may involve pushing a button, twisting, or clicking. A non-limiting example of an active needle shield mechanism 54 included in the BD INSYTE AUTO-GUARD™ BC shielded IV catheter. A non-limiting example of a passive needle shield mechanism 54 is the BD NEXIVA™ Closed IV Catheter System.

In some embodiments, when the user partially withdraws the needle 26 from the catheter adapter 12 such that the tip 24 of the needle 26 is disposed between the distal end of the catheter 14 and the septum 18, the lubricant 48 disposed within the gaps may prevent blood disposed on an outer surface of the tip 24 from penetrating the septum 18 through the slit 46. In some embodiments, the user may partially withdraw the needle 26 from the catheter adapter 12 such that the tip 24 of the needle 26 is disposed between the distal end of the catheter 14 and the septum 18. In these and other embodiments, the user may partially withdraw the needle 26 the needle shield mechanism 54, which may be is passive. In some embodiments, an example passive needle shield mechanism 54 may include a safety clip 56, which may be removed from the catheter adapter 12 in response to withdrawal of the needle 26 in a proximal direction from at least a portion of the catheter adapter 26 and the tip 24 being shielded within the safety clip 56.

FIGS. 6A-6B also illustrate an example needle hub 58, according to some embodiments. In some embodiments, when the needle 26 is partially withdrawn from the catheter adapter 12, a cross-section of the catheter adapter 12, the slit 46, and the needle 26 may be the same as or similar to FIG. 2B or 3B. As illustrated in FIG. 6C, when the lubricant 48 is disposed within the gaps, the lubricant 48 may also be disposed on other surfaces of the septum 18, such as, for example, the distal face or the proximal face.

Referring now to FIGS. 1-6, in some embodiments, an example method of manufacturing the catheter assembly 10 to prevent blood leakage through the septum 18 when the needle 26 is disposed within the slit 46 of the septum 18 may include providing the lubricant 48 within the gaps disposed between the outer surface of the needle 26 and the slit 46 of the septum. In some embodiments, providing the lubricant 48 within the gaps disposed between the outer surface of the needle 26 may include applying the lubricant 48 to the outer surface of the needle 26 prior to insertion of the needle 26 into the slit 46 of the septum 18 and/or inserting the lubricated needle 26 distally through the slit 46 of the septum 18. In some embodiments, in response to insertion of the lubricated needle 26 distally through the slit 46 of the septum 18, the lubricant 48 may be deposited within the gaps. In some embodiments, in response to insertion of the lubricated needle 26 distally through the slit 46 of the septum 18, at least a portion of the lubricant 48 may be transferred from the needle 26 to the gaps due to contact between the lubricant 48 on the needle 26 and the slit 46.

In some embodiments, applying the lubricant 48 to the outer surface of the needle 26 prior to insertion of the needle 26 into the slit 46 of the septum 18 may include applying the lubricant 48 to a portion of the outer surface of the needle 26. In some embodiments, the portion of the outer surface of the needle 26 may be configured to be disposed within the slit 46 of the septum 18 when the needle 26 is in the insertion position for insertion into the patient. In some embodiments, the needle 26 may extend beyond a distal end of the catheter 16 when the needle 26 is in the insertion position.

In some embodiments, the catheter assembly 10 may include the septum actuator 50, which may be configured to penetrate the septum 18 in response to insertion of the medical device 54 into the proximal end of the catheter adapter 12. In some embodiments, providing the lubricant 48 within the gaps disposed between the outer surface of the needle 26 and the slit 46 of the septum 18 may include applying the lubricant 48 to a distal tip 52 of the septum 18 actuator prior to insertion of the septum actuator 50 at least partially into the slit 46 of the septum 18 and/or inserting the lubricated septum actuator 50 at least partially into the septum 18. In some embodiments, in response to inserting the lubricated septum actuator 50 into the septum, the lubricant 48 may be deposited within the slit 46. In some embodiments, in response to movement of the septum actuator 50 at least partially through the slit 46, at least a portion of the lubricant 48 may be transferred to the gaps due to contact between the lubricant 48 on the septum actuator 50 and the slit 46.

In some embodiments, providing the lubricant 48 within the gaps disposed between the outer surface of the needle 26 and the slit 46 of the septum 18 may include dispensing the lubricant 48 within the slit 46 of the septum 18 prior to insertion of the septum 18 into the lumen 14 of the catheter adapter 12.

In some embodiments, a method of operating the catheter assembly 10 may include inserting the needle 26 of the catheter assembly 10 into the vasculature of the patient. In some embodiments, in response to inserting the needle 26 into the vasculature of the patient, blood flashback may occur between the outer surface of the needle 26 and an inner surface of the catheter 16. In some embodiments, a notch of the needle 26 disposed within the catheter 16 may allow the blood flashback. In some embodiments, the lubricant 48 disposed within the gaps may prevent the blood flashback from penetrating the septum 18 when the needle 26 is disposed within the slit 46 of the septum 18.

In some embodiments, the method of operating the catheter may further include partially withdrawing the needle 26 with respect to the catheter adapter 12 such that the tip 24 of the needle 26 is disposed between a distal end of the catheter 16 and the septum 18. In these and other embodiments, the needle 26 may be moved proximally and partially through the needle shield mechanism 54, which may be passive. In some embodiments, the needle 26 may not be partially withdraw with respect to the catheter adapter 12 when the catheter system 10 includes an active needle shield mechanism 54, as this may pose a danger of needle exposure. In these and other embodiments, the needle 26 may extend through the septum 18 when the needle 26 is partially withdrawn, and the lubricant 48 disposed within the gaps may prevent blood disposed on an outer surface of the tip 24 of the needle 26 from penetrating the septum 18.

The present invention may be embodied in other specific forms without departing from its structures, methods, or other essential characteristics as broadly described herein and claimed hereinafter. The described embodiments and examples are to be considered in all respects only as illustrative, and not restrictive. Although implementations of the present inventions have been described in detail, it should be understood that the various changes, substitutions, and alterations could be made hereto without departing from the spirit and scope of the invention.

The invention claimed is:

1. A method of manufacturing a catheter assembly to prevent blood leakage through a septum of a catheter assembly when a needle is disposed within a slit of the septum, comprising:

providing a lubricant within a plurality of gaps disposed between an outer surface of the needle and the slit of the septum, wherein the septum is disposed within a lumen of a catheter adapter, wherein a catheter extends distally from a distal end of the catheter adapter, wherein providing the lubricant within the plurality of gaps disposed between the outer surface of the needle and the slit of the septum comprises:

applying the lubricant to the outer surface of the needle prior to insertion of the needle into the slit of the septum; and inserting the lubricated needle directly through the slit of the septum in a distal direction toward a distal tip of the catheter, wherein in response to insertion of the lubricated needle directly through the slit of the septum and movement of the lubricated needle in the distal direction toward the distal tip of the catheter while the lubricated needle is in contact with septum, the lubricant is deposited within the plurality of gaps.

2. The method of claim 1, wherein the lubricant is a high viscosity lubricant having a viscosity greater than 1,000 centipoise.

3. The method of claim 1, wherein applying the lubricant to the outer surface of the needle prior to insertion of the needle into the slit of the septum comprises applying the lubricant to a portion of the outer surface of the needle, wherein the portion of the outer surface of the needle is configured to be disposed within the slit of the septum when the needle is in an insertion position for insertion into the patient.

4. The method of claim 1, wherein the slit is a Y-shaped slit, wherein the plurality of gaps includes exactly three gaps.

5. The method of claim 1, wherein the slit is a linear slit, wherein the plurality of gaps includes exactly two gaps.

6. The method of claim 1, wherein the lubricant comprises a water insoluble lubricant.

7. The method of claim 1, wherein the lubricant comprises an oil lubricant, wherein the oil lubricant comprises polydimethyl siloxane, polytrifluoropropylmethyl siloxane, or a copolymer of dimethylsiloxane and trifluoropropylmethylsiloxane.

\* \* \* \* \*